United States Patent
Yamane

(10) Patent No.: US 8,414,478 B2
(45) Date of Patent: Apr. 9, 2013

(54) ENDOSCOPIC ASPIRATION DEVICE

(75) Inventor: Kenji Yamane, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 867 days.

(21) Appl. No.: 12/392,806

(22) Filed: Feb. 25, 2009

(65) Prior Publication Data

US 2009/0216084 A1    Aug. 27, 2009

(30) Foreign Application Priority Data

Feb. 26, 2008   (JP) .................................. 2008-044403
Feb. 29, 2008   (JP) .................................. 2008-048955

(51) Int. Cl.
*A61B 1/12*      (2006.01)

(52) U.S. Cl. ....................................... 600/159; 600/158

(58) Field of Classification Search .......... 600/154–159, 600/103, 104, 106, 118, 125; 239/581.1; 403/322.2; 604/6.1, 33, 99.01–99.04, 167.03–167.04, 604/167.06

See application file for complete search history.

(56) References Cited

U.S. PATENT DOCUMENTS

| 5,257,773 | A | 11/1993 | Yoshimoto et al. |
| 6,908,429 | B2 | 6/2005 | Heimberger |
| 2004/0260151 | A1* | 12/2004 | Akiba ........................... 600/159 |

FOREIGN PATENT DOCUMENTS

EP        1 346 681 A2    9/2003

* cited by examiner

*Primary Examiner* — Matthew J Kasztejna
*Assistant Examiner* — Kevin G Barry, III
(74) *Attorney, Agent, or Firm* — Birch, Stewart, Kolasch & Birch, LLP

(57) ABSTRACT

An endoscopic aspiration device is mounted on a manipulating head of an endoscope, from which an elongated insertion rod member is extended forward, the endoscopic aspiration device being composed of a valve casing which is mounted on the manipulation head in communication with an aspiration passage running through the insertion rod member, and a valve assembly unit including a valve member, a valve guide member and a connector member attached to the valve guide member to communicate same with a proximal aspiration passage on the side of a suction source. The valve member is put in a sliding displacement along the valve guide member to bring the aspiration passage into and out of communication with the proximal aspiration passage on the side of a suction source. The valve guide member is coupled with the valve casing through a coupling mechanism which permits to turn the valve assembly unit on and relative to the manipulating head. The coupling mechanism is arranged to perform a function of coupling and uncoupling the valve guide unit with and from the valve casing, and a function of locking the valve guide member in the valve casing to prevent spontaneous dislodgement from the latter.

8 Claims, 14 Drawing Sheets

ENDOSCOPIC ASPIRATION DEVICE

TECHNICAL FIELD

This invention relates to an endoscopic aspiration device to be used on an endoscope for aspirating internal filth and body fluids from a body cavity.

TECHNICAL BACKGROUND

Generally, an endoscope is composed of a manipulating head and an elongated insertion instrument which is extended forward from the manipulating head for introduction into a body cavity in need of an endoscopic examination or treatment. In endoscopic examinations and treatments, an aspiration mechanism on an endoscope is resorted to for the purpose of observing an intracavitary site of interest in a clearly visible state. Namely, in case an intracavitary site under observation or treatment is covered with internal filth or body fluids like blood to such a degree as to make it difficult to observe the intracavitary site in question clearly, an aspiration mechanism is turned on to suck out covering internal filth and body fluids. In this regard, it has been the usual practice to utilize as an aspiration passage a tool introduction channel which is provided on an endoscope for introduction of forceps or other surgical instruments into a body cavity. In some cases, an aspiration passage is provided separately from a tool introduction channel. Any way, an endoscopic aspiration device including an aspiration valve and a valve operating member is mounted on a manipulating head of an endoscope. The aspiration valve is connectible to a proximal aspiration passage from a suction source, so that aspiration can be carried out for a necessary time period by manipulation of the aspiration valve operating member.

By the way, not only aspiration passages including a tool introduction channel of an endoscope and interiors of an aspiration valve but also interiors of a proximal aspiration passage on the side of a suction source unavoidably get contaminated by the use of an endoscopic aspiration device. Therefore, all of contaminated aspiration passages in transit have to be completely washed and disinfected before using the endoscope again. However, an aspiration valve which is adapted to bring aspiration passages into and out of communication with a proximal aspiration passage on the side of a suction source is complicate in construction, so that it has been extremely difficult to completely wash the entire routes of aspiration through and to and from an aspiration valve which is mounted on a manipulating head of an endoscope.

With a view to solving the problem as mentioned above, for example, Patent Literature 1 below discloses an aspiration valve which is improved in washability. In Patent Literature 1, an aspiration passage which is provided internally of an elongated insertion rod member as far as an opening at a fore distal end of the insertion rod member is connected with a proximal aspiration passage on the side of a suction source at a point on a manipulating head of the endoscope. In order to connect and disconnect the aspiration passage to and from the proximal aspiration passage, a proximal end of the aspiration passage is connected to a valve casing within a housing of the manipulating head, and an external valve assembly unit is disconnectibly connected to the valve casing. The external valve assembly unit is constituted by a valve guide member which is adapted to be disconnectibly connected to the valve casing, and a valve member to be slidably fitted in the valve guide member. A connector pipe is provided at a lateral side of the valve guide member for disconnectibly connecting thereto a proximal aspiration passage on the side of a suction source.

One end of the valve member, i.e., an end away from a valve body at the other end, is arranged to serve as an aspiration trigger portion which is designed to be manipulated by a finger of an operator's hand which grips the manipulating head of the endoscope. The valve body is located in the valve casing, normally blocking communication between the aspiration passage and proximal aspiration passage. As the aspiration trigger portion is pushed in, the valve body is caused to slide along inner surfaces of the valve casing to open the communication between the aspiration passage and the proximal aspiration passage. As a result, the vacuum pressure from the proximal aspiration passage comes to prevail in the aspiration passage to apply a suction force to an opening at the distal end of the insertion rod member.

The aspiration takes an internal route through the insertion rod member and as far as the manipulating head of the endoscope, and then takes an external route which is led out from a housing of the manipulating head. A flexible tube of a proximal aspiration passage, i.e., a passage on the side of a suction source, is connected to a connector pipe which is extended out from the above-mentioned valve guide, which is projected on the housing of the manipulating head. When an operator grips the manipulating head in his or her hand to operate the endoscope, however, the connector pipe and the flexible proximal aspiration passage are often found obstructive of the operation of the endoscope. For this reason, the valve assembly unit is arranged to be turnable relative to the valve casing, permitting to turn the connector pipe and the flexible proximal aspiration passage out of the way of manipulation of the endoscope.

The above-mentioned valve assembly unit is disconnectible from the valve casing. After each use, the valve assembly unit is dismantled from the valve casing and a cleaning brush is inserted into the aspiration passage for washing same completely. The flexible proximal aspiration passage which is connected to the valve assembly unit and connector pipe can be reused after washing or may be simply discarded and replaced by a new one.

PRIOR ART LITERATURE

[Patent Literature 1] Japanese Laid-Open Patent Application 2007-252589

SUMMARY OF THE INVENTION

Problem(s) Solved by the Invention

As mentioned hereinbefore, in Patent Literature 1 above, for the purpose of improving washability, a proximal aspiration passage on the side of a suction source is led out from a valve assembly unit in a valve casing, instead of taking a route through a universal connection cable which is connected to a manipulating head of the endoscope. The aspiration valve employed in Patent Literature 1 is improved in washability but still has a problem. Namely, the valve assembly unit which is detachably connectible to the valve casing on the manipulating head of an endoscope in such a way that a connector pipe and proximal aspiration passage on the side of a suction source can be turned to a position out of the way of manipulations of the endoscope, using a coupling mechanism which is adapted to lock the valve assembly unit in the valve casing by engagement of a stopper protuberance which is provided on the part of the valve casing, with a interlocking projection which is provided on the part of the valve guide member and adapted to ride over the stopper protuberance on the side of the valve casing.

In order to prevent spillage of internal filth and body fluids like blood which are being aspirated through an aspiration passage, the valve guide member should be coupled with the valve casing in such a way as to preclude possibilities of dislodgement of the valve guide member from the valve casing on the manipulating head of the endoscope. For this purpose, the valve guide member needs to be connected fast to the valve casing, for example, by increasing the height of the interlocking projection and stopper protuberance to such a degree which is sufficient enough for preventing fall-off or slip-off of the valve guide member. However, it is very likely that the use of higher interlocking projection and stopper protuberance will make it difficult to extract the valve guide member from the valve casing for washing purposes each time after using an endoscope.

In view of the above-discussed problem with the prior art, it is an object of the present invention to provide an endoscopic aspiration device having a pipe of a proximal aspiration passage on the side of a suction source detachably connected to an aspiration valve, a valve assembly unit of the aspiration valve being coupled with and uncoupled from a valve casing on a manipulating head of an endoscope in a facilitated manner and securely locked in a coupled position within the valve casing once fitted into the latter.

It is another object of the present invention to provide an endoscopic aspiration device which is adapted to retain a valve assembly unit securely in position within a valve casing free of possibilities of dislodgement from the valve casing while manipulating an endoscope, the valve assembly unit however being easily extractable from the valve casing, for example, when it becomes necessary to wash the valve assembly unit after use.

Means for Solving Problem(s)

According to the present invention, in order to achieve the above-stated objectives, there is provided an endoscopic aspiration device for use on a manipulating head of an endoscope, to which a proximal end of an elongated insertion rod member is connected, the endoscopic aspiration device comprising a valve casing provided on the manipulating head in communication with an aspiration passage leading to a fore distal end of the insertion rod member, and a valve assembly unit composed of an assembly of a valve member and a valve guide member having a connector member extended out for connection to a proximal aspiration passage on the side of a suction source, the valve member being put in a sliding displacement along the valve guide member to bring the aspiration passage into and out of communication with the proximal aspiration passage, characterized in that the endoscopic aspiration device comprises: a coupling mechanism provided between the valve casing and the valve guide member of the valve assembly unit and adapted to couple the valve guide member with the valve casing in such a way as to permit the valve assembly unit to make turns about a center axis of the valve casing on the manipulating head; and the coupling mechanism including a coupling/uncoupling mechanism with a function of bringing the valve guide member of the valve assembly unit into and out of fitting engagement with the valve casing, and a lock-in mechanism with a function of retaining the valve guide member in a coupled state within the valve casing, preventing spontaneous dislodgement of the valve assembly unit from the valve casing.

A valve assembly unit which is largely composed of a valve guide member and a valve member is detachably fitted in a valve casing which is provided on the side of a manipulating head of an endoscope. In this regard, arrangements should be made to prevent spontaneous dislodgement of the valve assembly unit from the valve casing. In order to prevent the valve assembly unit from easily coming off the valve casing, it should be securely locked in the valve casing while the endoscope is in use including an aspirating operation. However, at the time of washing the endoscope after use, the valve assembly unit including the proximal aspiration passage on the side of a suction source should be easily uncoupled and dismantled from the valve casing.

A valve guide member of a valve assembly unit should be coupled with a valve casing through a coupling/uncoupling mechanism which permits to uncouple the valve guide member from the valve casing whenever necessary. However, if the valve assembly unit is dislodged from the valve casing while the endoscope is in use, aspirated body fluids or other unsanitary fluids will spill out from the valve casing. Therefore, when an endoscope is being manipulated, the valve assembly unit should be securely and stably locked in the valve casing in an operatively coupled state.

For this purpose, a coupling/uncoupling function is performed by an arcuate segmental guide groove which is provide on one of fitting portions of the valve casing and valve guide member for engagement with a locking projection on the other one of the fitting portions of the valve casing and valve guide member, and an introductory groove which is provided contiguously to an entrance to the guide groove for introduction of the locking projection into the latter. A lock-in function is performed by limiting a rotational angle of the valve guide member relative to the valve casing to a predetermined angular range thereby keeping the locking projection off an axially overlapping position on the introductory groove.

In this regard, normally the guide groove and introductory groove are provided on the inner periphery of the valve casing, while the locking projection is provided on the outer periphery of the valve guide member. The connector member which is connected to the valve guide is constituted by a rigid pipe and projected radially outward from a lateral side of the valve guide member of the valve assembly unit. The connector member can be turned about a center axis of the valve assembly unit.

Although the connector member which is turnable about the valve assembly unit, it does not need to be turned through 360 degrees during manipulation of an endoscope. From the standpoint of maneuverability of the endoscope, a proximal aspiration passage which is connected with the connector member should be extended in a direction away from the body of an operator. Therefore, in a case where the connector member is extended to the left of a manipulating head of the endoscope, arrangements can be made for a lock-in function in such a way as to prevent the locking projection from coming into alignment with the introductory groove. The connector member is not turned to the right of the manipulating head of the endoscope while manipulation of the latter, but the locking projection can be brought into alignment with the introductory groove to effectuate a coupling/uncoupling function as soon as the connector member is turned to that direction.

Various manual operating members are provided on a housing of the manipulating head, including a push button switch. Thus, a bush button can be located on the housing of the manipulating head on the proximal side of the valve casing to utilize same as part of a lock-in mechanism. The push button is projected on the housing of the manipulating head to such a height that it comes into interference with the connector member when the valve guide is turned in the valve casing in a coupled state, limiting the angular range of the turn of the valve guide member short of a position where the locking projection is axially aligned with the introductory groove. When the push button is depressed to permit passage thereover of the connector member, the connector member can be turned beyond the above-mentioned angular range to bring the locking projection into alignment with the introductory groove to effectuate the coupling/uncoupling function. Thus, arrangements are made to bring the locking projection into alignment with the introductory groove at a position which partly coincides with a position where the connector member is overlapped with the push button.

When a first rotation limit point for the valve assembly unit is set at one end of the arcuate guide groove where the connector member comes into abutment against the push button, a second rotation limit point is set at the other end of the guide groove by providing a stopper wall at the other end. Thus, the connector member is can be put in a sliding displacement in the guide groove in an angular range which is defined on one side of the introductory groove by the first and second rotation limit points, effectuating the lock-in function. On the other hand, when the locking projection is located in an angular range on the other side of the introductory groove, the coupling/uncoupling function is effectuated to permit coupling and uncoupling of the valve assembly unit into and out of the valve casing.

A stationary flange member is provided at an upper end of the valve casing which is projected outward of the manipulating head, for abutting engagement with a detachable flange portion on the side of the valve guide member. In order to hold the stationary and detachable flanges fast to each other, a resilient holder ring is fitted on. The holder ring which is formed of a resilient material is in the form of a split ring an axial split portion to present C-shape in cross section.

A stationary flange may be formed integrally with the valve casing if desired. Alternatively, it can be formed by threading a nut on an external screw which is formed around a projected end of the valve casing. On the other hand, a detachable flange portion can be formed on the valve guide member contiguously to a fitting portion to put in fitting engagement in the valve casing. In order to hold the stationary and detachable flanges fast to each other, gripper portions in the form of arcuate ribs are formed at two axially spaced positions on the inner periphery of the holder ring. Namely, the flanges are gripped between lower and upper gripper ribs which are spaced apart by a distance corresponding to a sum of thicknesses of the two flanges.

The lower gripper portions are formed at the lower end of the holder ring and provided with a tapered guide surface which is gradually diverged toward the lower end of the holder ring. Under the guidance of the tapered guide surface, the valve assembly unit having the holder ring fitted thereon can be smoothly fitted in and coupled with the valve casing. The resilient holder ring, which is split in C-shape, can hold the two flanges securely and stably in a gripped state, effectively contributing to the performance of the lock-in function mentioned above. Preferably, expander tabs are provided on the outer periphery of the holder ring in the vicinity of the split portion to facilitate its detachment from the valve guide member in performing the coupling/uncoupling function.

In case the connector member is connected to a connection port at a lateral side of the valve guide member as mentioned above, it is preferred to provide flanges on the valve guide member on the upper and lower sides of the connection port of the connector member. In this instance, the flange on the lower side serves as the detachable flange portion, while the flange on the upper side serves as a trigger mount portion. In addition to the above mentioned upper and lower gripper portions, preferably a third gripper portions is provided on the inner periphery of the holder ring, the third gripper portion being brought into engagement with the upper flange to hold the valve guide member in a more stabilized state prior to bringing the holder ring into abutment against the valve casing.

The above and other objects, features and advantages of the present invention will become apparent from the following particular description of preferred embodiments shown in the accompanying drawings. Needless to say, the invention is not limited to particular forms exemplified in the drawings.

DESCRIPTION OF PREFERRED EMBODIMENTS

Hereafter, with reference to the accompanying drawings, the invention is described more particularly by way of its preferred embodiments. In the accompanying drawings, shown in FIGS. 1 through 9 is a first embodiment, and shown in FIGS. 10 through 14 is a second embodiment of the present invention.

Figure 1:
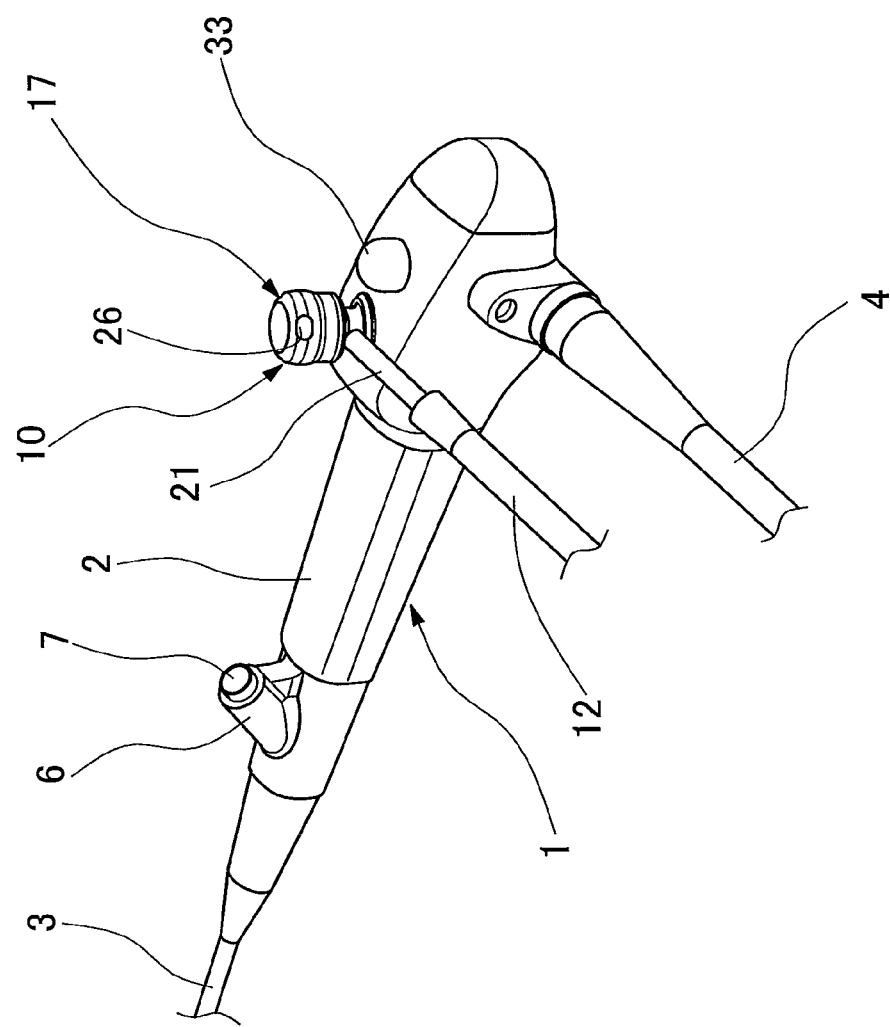
FIG. 1 is a perspective outer view of a manipulating head of an endoscope in a first embodiment of the invention.
Figure 2:
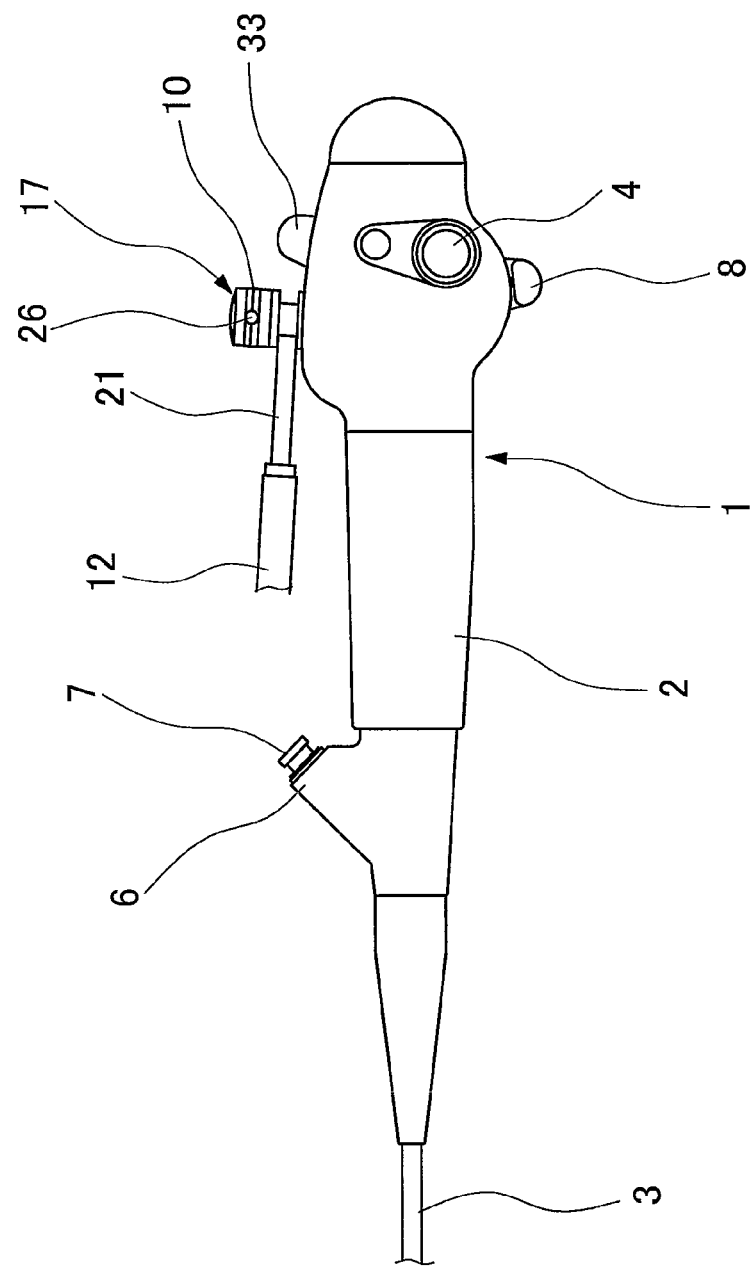
FIG. 2 is a schematic front view of the manipulating head in FIG. 1.
Figure 3:
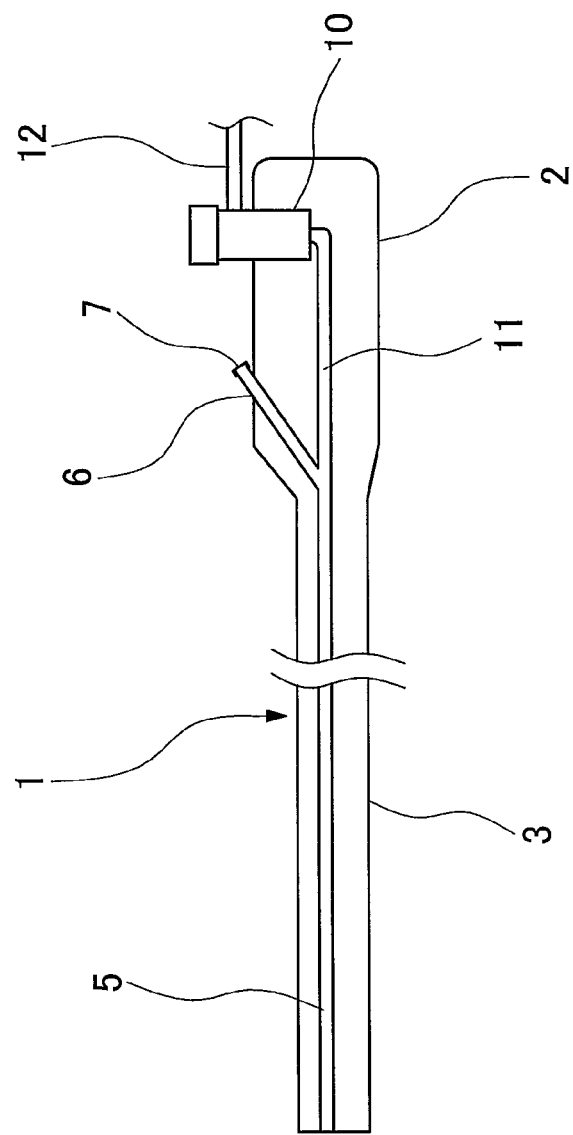
FIG. 3 is a schematic view showing layout of endoscopic aspiration passages.

FIGS. 1 and 2 show a manipulating head of an endoscope to which the present invention is applicable, while FIG. 3 schematically shows a layout of endoscopic aspiration passages. In these figures, indicated at 1 is an endoscope proper, which is composed of a manipulating head 2 and an elongated insertion rod or insertion rod member 3. A universal connection cable 4 is led out from the manipulating head 2. A tool introduction channel 5 is provided internally of the insertion rod 3 as far as an exit opening which is opened at the fore distal end of the insertion rod for introduction of a surgical or bioptic tool into a body cavity. The proximal end of the tool introduction channel 5 is opened to a tool entrance way 6 on a housing of the manipulating head 2. Normally, the tool entrance way 6 is closed by a plug member 7.

The above-mentioned tool introduction channel 5 is also used as an aspiration passage and branched off an aspiration passage 11 at a junction point internally of the manipulating head 2. On the other hand, the aspiration passage 11 is connected to an aspiration device 10 including an aspiration valve and a valve operating means. Connected to the aspiration device 10 is a fore end of a flexible proximal aspiration passage, i.e., a proximal aspiration passage 12 on the side of a suction source (not shown). The aspiration device 10 controls connections of the proximal aspiration passage 12, bringing the proximal aspiration passage 12 into communication with either the atmosphere or the aspiration passage 11 as it is manipulated by a finger of an operator's hand which grips the manipulating head 2.

Figure 4:
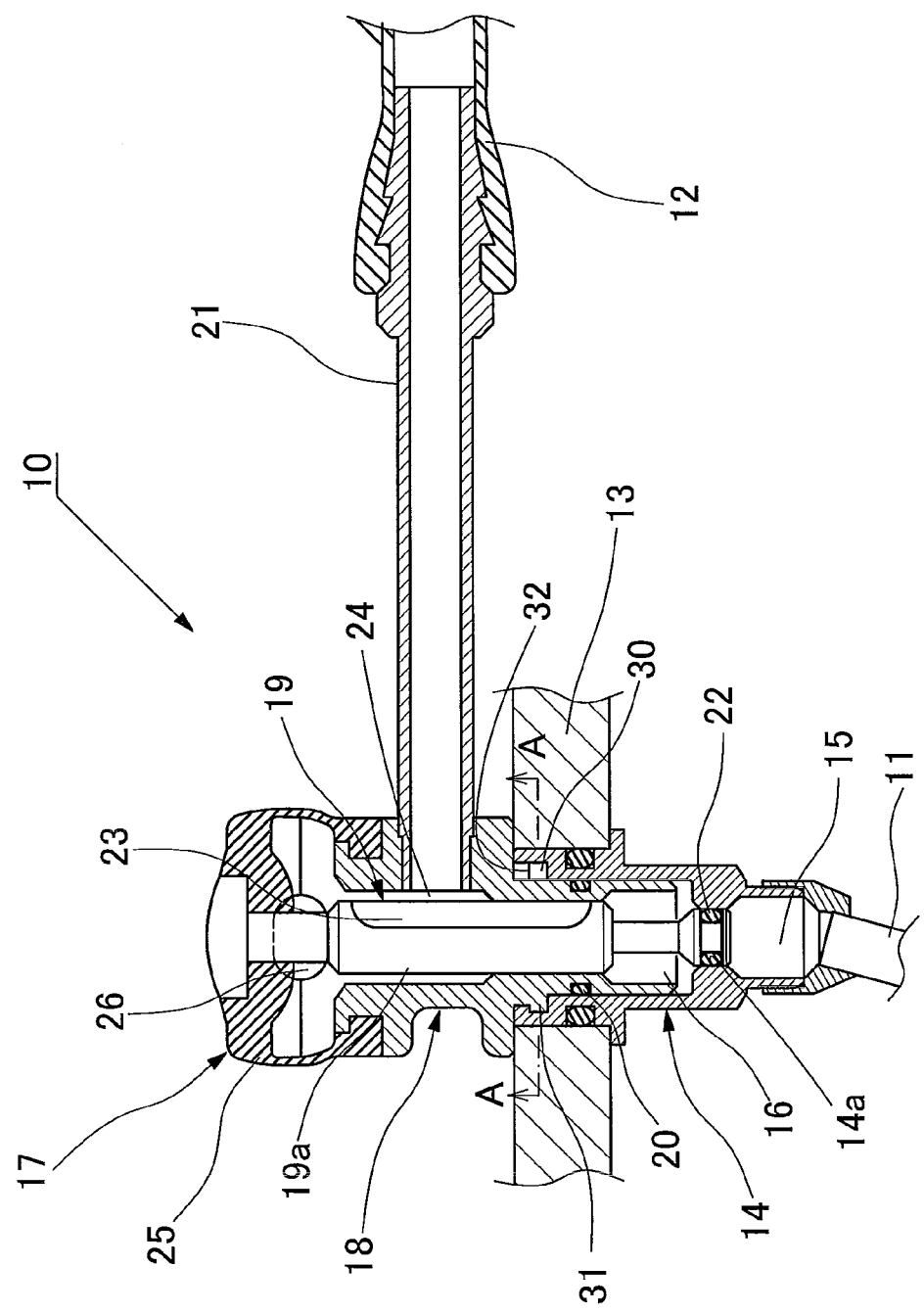
FIG. 4 is a schematic sectional view of an endoscopic aspiration device according to the invention.

Shown in FIG. 4 are more details in construction of the aspiration device 10. As seen in that figure, a valve casing 14 of the aspiration device 10 is fixedly fitted in a housing 13 of the manipulating head 2 of the endoscope. An aspiration passage 11 is connected to a lower bottom end of the valve casing 14 (in the following description, a direction inward of the housing 13 of the manipulating head 2 is described as a downward direction and a direction outward of the housing 13 is described as an upward direction for the convenience of explanation). The valve casing 14 is provided with a constricted wall portion of a reduced diameter on and around its inner periphery, providing a sliding surface 14a over a predetermined length in the axial direction. By a valve member which will be described hereinlater, the valve casing 14 is divided into a first chamber 15 and a second chamber 16 on the lower and upper sides of the sliding surface 14a of the constricted wall portion, respectively.

Fitted in the valve casing 14 is a valve assembly unit 17 which is composed of a valve guide member 18 and a valve member 19. The valve guide member 18 is fitted in the second chamber 16 of the valve casing 14, and a seal member 20 is interposed between the valve guide member 18 and the valve casing 14. The valve member 19 is fitted in the valve guide member 18 and slidable linearly in the axial direction under the guidance of inner peripheral surfaces of the valve guide member 18. A rigid connector pipe 21 is fitted into the valve guide member 18 from a lateral direction at an upper position of the latter, and a proximal aspiration passage 12 from a suction source is detachably connected to an outer end of the connector pipe 21. That is to say, the connector pipe 21 is located on one lateral side of the valve guide member 18 substantially at right angles relative to the longitudinal axis of the latter, permitting to connect the proximal aspiration passage 12 on the side of the suction source from a lateral direction of the manipulating head 2 of the endoscope.

The valve member 19 which is fitted in the valve guide member 18 is composed of a body shaft 19a which is extended in the axial direction of the valve guide member 18 and provided with a resilient valve portion 22 at its lower end in sliding engagement with the sliding surface 14a on the part of the valve casing 14. The body shaft 19a is arranged to have a predetermined axial length, and an annular passage 24 is formed between outer peripheral surface of the body shaft 19a and inner peripheral surface of the valve guide member 18 in communication with the connector pipe 21. An intercommunicating passage 23 which is provided on the body shaft 19a of the valve member 19 is constantly held in communication with the annular passage 24.

Provided at an upper or outer end of the body shaft 19a is a dome-like trigger member 25 which is formed of a resilient material and provided with an opening 26 in a girder wall portion in communication with the atmosphere. As the aspiration trigger member 25 is pressed in or out with a finger, the valve portion 22 is slid along the sliding surface 14a of the valve casing 14 to bring the first and second chambers 15 and 16 into or out of communication with each other, while covering or uncovering the opening 26 to turn on and off the aspiration device 10. By way of the aspiration trigger member 25, the valve guide member 18 and valve member 19 are connected with each other.

Normally, the aspiration device 10 is retained in an off-position shown in FIG. 4. In this position, communication between the first and second chambers 15 and 16 is blocked by the valve portion 22 of the valve member 19, and the connector pipe 21 is communicated with the atmosphere through the annular passage 24 and the opening 26 in the aspiration trigger member 25. Thus, no suction force is applied to the aspiration passage 11. As the aspiration trigger member 25 is pushed inward from the off-position, the communication with the opening 26 is blocked and the valve portion 22 is moved downward to bring the first and second chambers 15 and 16 into communication with each other. As a consequence, the connector pipe 21 which is connected to the proximal aspiration passage 12 on the side of the suction source is brought into communication with the aspiration passage 11 via the annular passage 24, intercommunicating passage 23 and the first and second chambers 15 and 16 to apply the suction force in the proximal aspiration passage 12 on the side of the suction source to the aspiration passage 11 to aspirate body fluids through an aspiration port at the fore distal end of the tool introduction channel 4 on the insertion rod member 3.

The endoscope 1 is used repeatedly and therefore needs to be washed after each use. Particularly, aspiration passages which are unavoidably subjected to contamination with body fluids or the like need to be washed completely and entirely. For this purpose, the valve assembly unit 17 is extractable from the valve casing 14, permitting to wash aspiration passages including the aspiration passage 11 and interiors of the valve casing 13 completely in a facilitated manner. On the other hand, the extracted valve assembly unit 17 may be reused after washing, but preferably it is discarded after a single use.

For manipulation of the endoscope 1, an operator grips the manipulating head 2 in his or her hand. The proximal aspiration passage 12 which is connected to the valve guide 18 of the valve assembly unit 17 by way of the connector pipe 21 may obstruct the manipulation of the endoscope 1 and therefore should preferably be put out of the way of endoscope manipulation. For this purpose, the valve assembly unit 17 is arranged to be able to turn about its longitudinal axis relative to the valve casing 14. Further, the connector pipe 21 can be easily turned into a different angular position around the aspiration device 10 by pushing same toward a desired angular position, followed by the flexible tube of the proximal aspiration passage 12 which is connected to the connector pipe 21. A seal member 20 is interposed between the valve guide member 17 and the valve casing 14, so that a turning force on the connector pipe 21 is met by a certain degree of resistance, which in turn contributes to retain the connector pipe 21 and the proximal aspiration passage 12 stably in a desired angular position.

Figure 5:
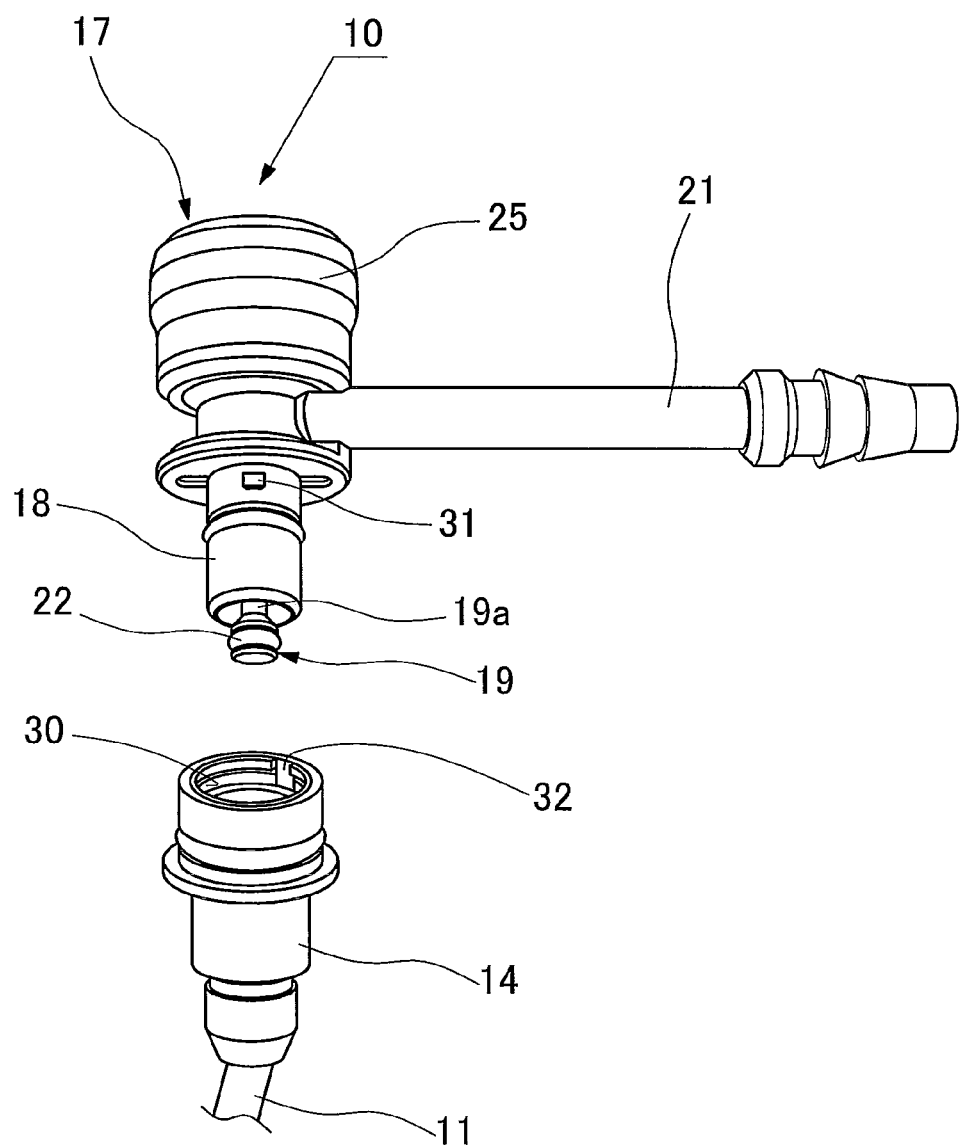
FIG. 5 is an exploded perspective view of the aspiration device of FIG. 4.
Figure 6:
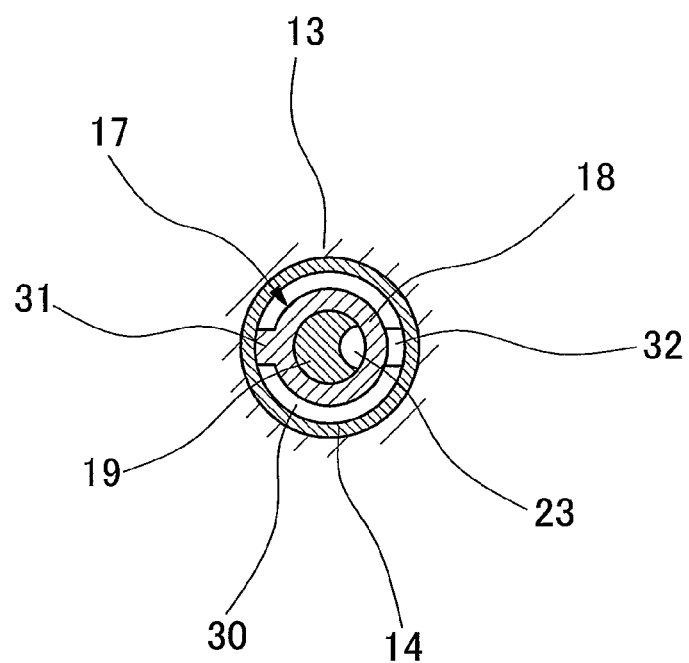
FIG. 6 is a cross section of the aspiration device, taken on line A-A of FIG. 4.

The valve assembly unit 17 is coupled with the valve casing 14 through a coupling mechanism as described below with reference to FIGS. 4, 5 and 6.

An annular guide groove 30 is formed around the inner periphery of the valve casing 14. On the other hand, a segmental locking projection 31 is formed around a girder of the valve guide member 18 and engaged with the guide groove 30 on the part of the valve casing 14 to prevent spontaneous dislodgement of the valve guide member 18 from the valve casing 14. This segmental locking projection 31 is slightly smaller than the guide groove 30 in thickness or width, and radially projected from the girder of the valve guide member 18 to a height which substantially corresponds to the depth of the guide groove 30. An introductory groove 32 of the same width and depth as the guide groove 30 is formed around the inner periphery of the valve casing 14 in contiguously overlapping relation with an entrance to the guide groove 30. This introductory groove 32 is opened to the upper end of the valve casing 14 at its outer side and communicated with an entrance portion of the guide groove 30 at the other or inner side.

At the time of assembling the valve guide member 18 into the valve casing 14 by fitting engagement with the latter, the segmental locking projection 31 on the valve guide member 18 is put into the guide groove 30 of the valve casing 14 by way of the open side of the introductory groove 32. Then, the valve guide member 18 is turned in the guide groove 30 until the segmental locking projection 31 is shifted to a radial position where it is locked in the guide groove 30 in the axial direction. At this time, as the segmental locking projection 31 is slid along the guide groove 30, the valve assembly unit 17 as a whole is turned relative to the valve casing 14 about the longitudinal axis of the latter. Thus, as long as the segmental locking projection 31 is in an axially locked position within the guide groove 30, the valve assembly unit 17 is securely retained in the valve casing 14 in such a way as to preclude possibilities of its dislodgement from the valve casing 14. Thus, the valve assembly unit 17 is detachably assembled with the valve casing 14 by a coupling/uncoupling function which is performed jointly by the guide groove 30, introductory groove 32 and segmental locking projection 31.

As the valve guide member 18 of the valve assembly unit 17 is turned within the valve casing 14, the valve assembly unit 17 can be dislodged from the valve casing 14 if the locking projection 31 is shifted to an axially aligned position relative to the introductory groove 32 on the side of the valve casing 14. During or immediately after an aspirating operation, for example, the entire paths of aspiration from the aspiration passage 11 to the proximal aspiration passage 12 on the side of a suction source are filled with body fluids or other aspirated internal filth, so that the aspirated body fluids can spill out through an opening of the valve casing 14 should the valve assembly unit 17 come off the valve casing 14. In order to prevent this, the turning angle of the valve assembly unit 17 is limited to a predetermined angular range during an aspirating operation by means of a rotation limiting mechanism, thereby preventing the segmental locking projection 31 from being turned as far as the position of the introductory groove 32.

As shown in FIG. 2, a universal connection cable 4 is led out from the manipulating head 2 of the endoscope. More particularly, compared with the insertion rod 2 which is extended out on the front side of the manipulating head 2, the universal connection cable 4 is led out from a left side of the housing 13 of the manipulating head 2. This is because normally the manipulating head 2 is gripped in a left hand of an operator who takes a position on the right side of the manipulating head 2. Therefore, the proximal aspiration passage 12 on the side of a suction source is necessarily extended leftward of the housing 13, that is, in a direction away from the body of an operator. If located on the right side, the proximal aspiration passage 12 will obstruct the manipulation of the endoscope to a considerable degree. Therefore, unless there is an exceptional reason, the connector pipe 21 is not located on the right side of the manipulating head 2.

Thus, the introductory groove 32 is formed on the inner periphery of the valve casing 14 in a position at the left side of the housing 13 of the manipulating head 2. Further, the segmental locking projection 31 on the side of valve guide member 18 is formed at a position virtually on the opposite side away from the side where the connector pipe 21 is extended out from the valve guide member 18. Accordingly, when coupling the valve assembly unit 17 with the valve casing 14, the proximal aspiration passage 12 is extended in a direction rightward of the manipulating head 2, namely, in an opposite direction relative to the universal connection cable 4. In this state, somehow an operator can manage to grip and manipulate the endoscope 1 but it is very likely that manipulation of the endoscope 1 is hindered by the connector pipe 21 and proximal aspiration passage 12 which present themselves as obstacles in the way of manipulation.

Therefore, when manipulating the endoscope 1, the valve assembly unit 17 is always turned to the left side to take a position leftward of the manipulating head 2, keeping the proximal aspiration passage 12 in that position in the course of manipulation of the endoscope 1, adjusting its angular position if necessary. Thus, while the endoscope 1 is being manipulated, there is no possibility of the locking projection 31 being turned as far as the position of the introductory groove 32, that is to say, the valve assembly unit 17 is securely locked in position in the valve casing 14 by a lock-in function performed by the locking projection 31 itself.

However, the above-mentioned lock-in function is effectual as long as the manipulating head 2 is gripped in an operator's hand. The limitation of rotational movement of the valve assembly unit 17 by the lock-in function becomes ineffectual when the endoscope 1 is put apart from an operator's body, for example, when put on a desk or when handed over to an assistant operator.

A number of manual operating members to be manipulated by an operator are provided on the manipulating head 2 of the endoscope 1. For example, as shown in FIG. 2, a nose angle control member 8 is provided on the manipulating head 2 for controlling an angle of an articular angling section in a fore end portion of the insertion rod member 3, in the fashion of remote control. Further, usually a push button switch 33 is provided on the manipulating head 1 to capture picture images of an intracavitary site under observation. This push button switch 33 is pushed by a finger of an operator's hand which grips the manipulating head 2. If desired, the push button switch 33 can be utilized to perform the lock-in function for the valve assembly unit 17.

Figure 7:
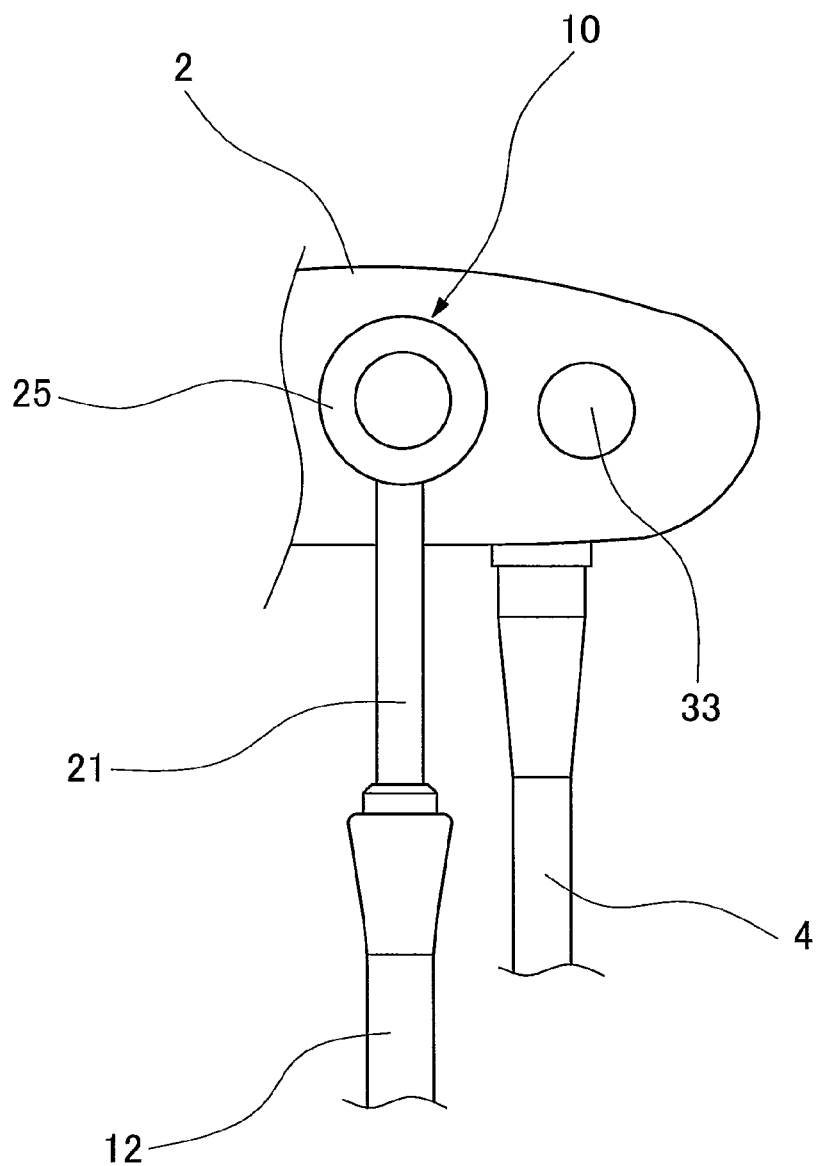
FIG. 7 is a schematic illustration explanatory of another example of a lock-in mechanism for preventing dislodgement of a valve assembly unit from a valve casing.
Figure 8:
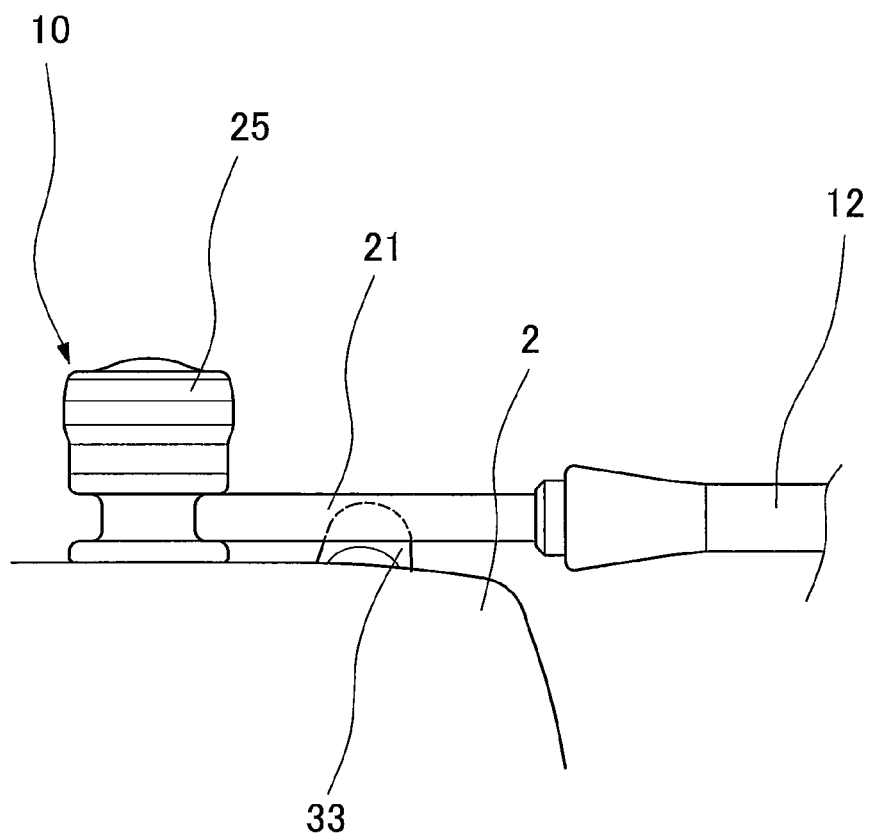
FIG. 8 is a schematic illustration explanatory of functions of the lock-in mechanism shown in FIG. 7.

For example, arrangements are made such that the connector pipe 21 comes to an overlapping position on the push button switch 33 when it is turned toward the proximal end as shown in FIG. 7. Further, as shown in FIG. 8, the push button switch 33 is projected on the housing 13 to an interfering height relative to the connector pipe 21. When depressed, the push button switch 33 is pushed down to a low position indicated by imaginary line in FIG. 8, permitting the connector pipe 21 to pass thereover.

With the arrangements as described above, when the locking projection 31 on the valve guide member 18 is located in an axially aligned position relative to the introductory groove 32 on the side of the valve casing 31 for the purpose of fitting the valve assembly unit 17 into the valve casing 14, at least part of the connector pipe 21 which is extended out from the valve guide member 18 is located in a position over the push button switch 33 on the casing 13. Namely, the introductory groove 32 of the valve casing 14 is provided in a position forward of the push button switch 33, while the locking projection 31 is located in a position under the connector pipe 21.

In this state, unless the push button switch 33 is depressed, the valve assembly unit 17 cannot be turned to a position where the locking projection 31 is axially aligned with the introductory groove 32. That is to say, there is no possibility of dislodgement of the valve assembly unit 17 from the valve casing 14 when the endoscope is being manipulated in an ordinary fashion or when the endoscope is not being manipulated. The valve assembly unit 17 can be extracted from the valve casing 14 by depressing the push button switch 33 and turning the valve guide member 18 to bring the connector pipe 21 to a position on the depressed push button switch 33.

Figure 9:
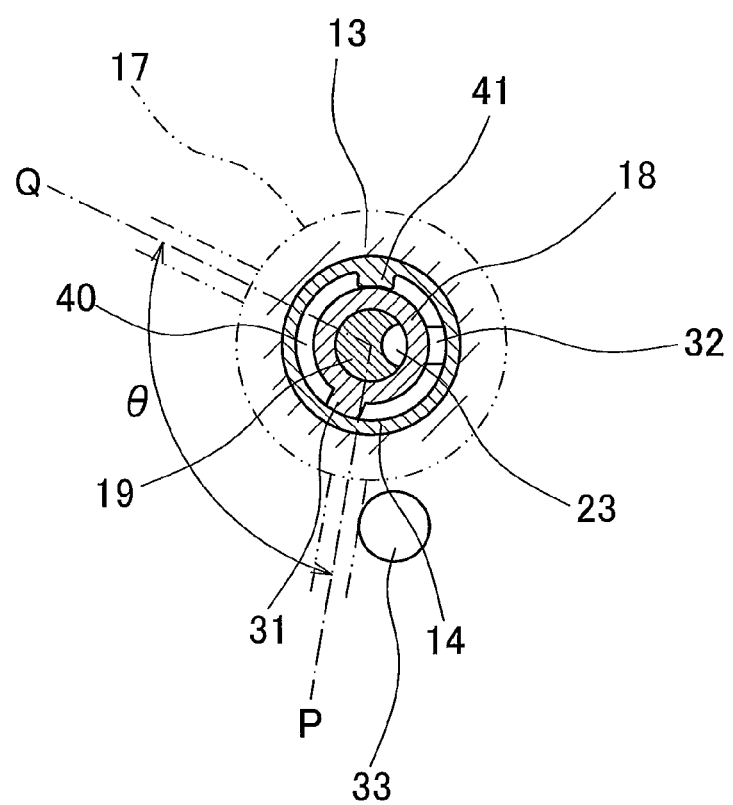
FIG. 9 is a schematic sectional view showing another example of the lock-in mechanism.

As described above, since an operator normally stands on the right side of the manipulating head 2, the operator will not feel inconvenience as long as the connector pipe 21 and the ensuing proximal aspiration passage 12 on the side of a suction source are located on the left side of the housing 13 of the manipulating head 2 because there will arise no necessity for turning them around to the right side of the housing 13 during manipulation of the endoscope. Accordingly, turn angles of the connector pipe 21 can be limited to the range of angle theta in FIG. 9. In this case, the position of the push button switch 33 is set at a first limit point P. Further, as shown in FIG. 9, an arcuate guide groove 40 is extended in a direction away from the first limit point P as far as a stopper wall 41. Thus, the locking projection 31 can be turned as far as the stopper wall 41 which is provided at the other end of the guide groove 40 to function as a second limit point Q.

Consequently, the valve guide member 17 is turnable only in a limited range, i.e., in the range between the first and second limit points P and Q on the left side of the manipulating head 2, namely, in the range of angle theta in FIG. 9. In this case, as indicated by imaginary line in FIG. 9, the introductory groove 32, serving to introduce the locking projection 31 of the valve guide member 17 into the guide groove 40, can be located at an arbitrary position in an angular range on the right side of the housing 13 between the first and second limit points P and Q, while the locking projection 31 is located in an angular range on the left side. By turning the locking projection 31 until it reaches an axially aligning position with the introductory groove 32, riding over the push button switch 33, the valve assembly unit 17 can be extracted from the valve casing 14.

Now, turning to FIGS. 10 through 14, there is shown a second embodiment of the invention. In this embodiment, a valve casing and a valve assembly unit are disconnectibly coupled with each other through a coupling mechanism with locking and unlocking functions.

Figure 10:
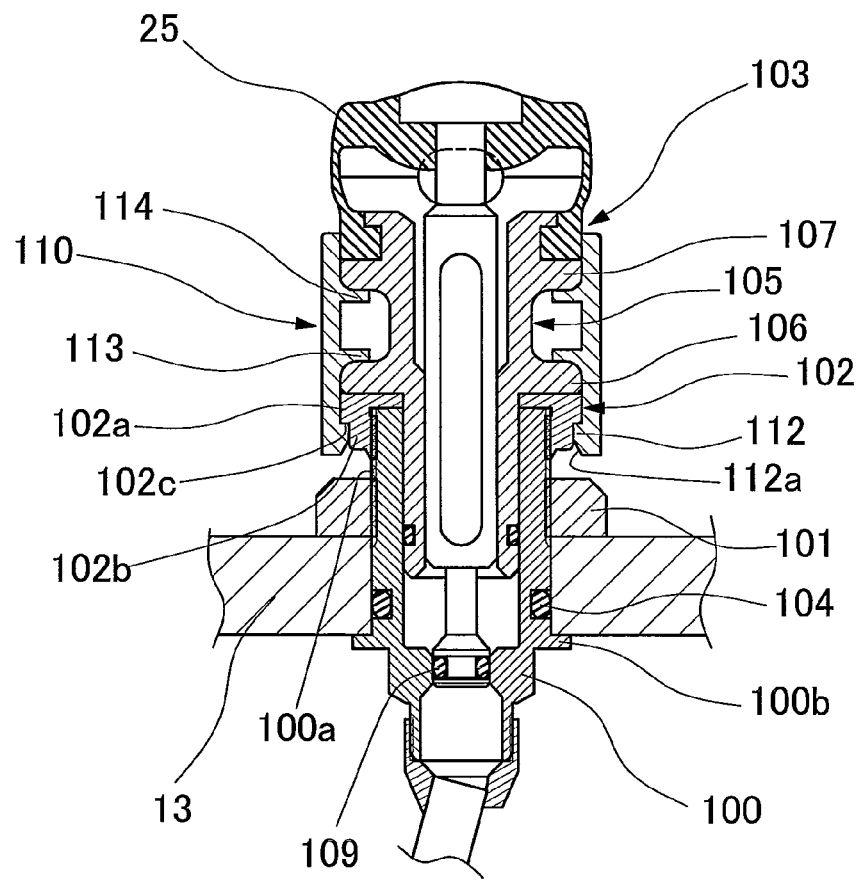
FIG. 10 is a schematic sectional view of an endoscopic aspiration device in a second embodiment of the invention.
Figure 11:
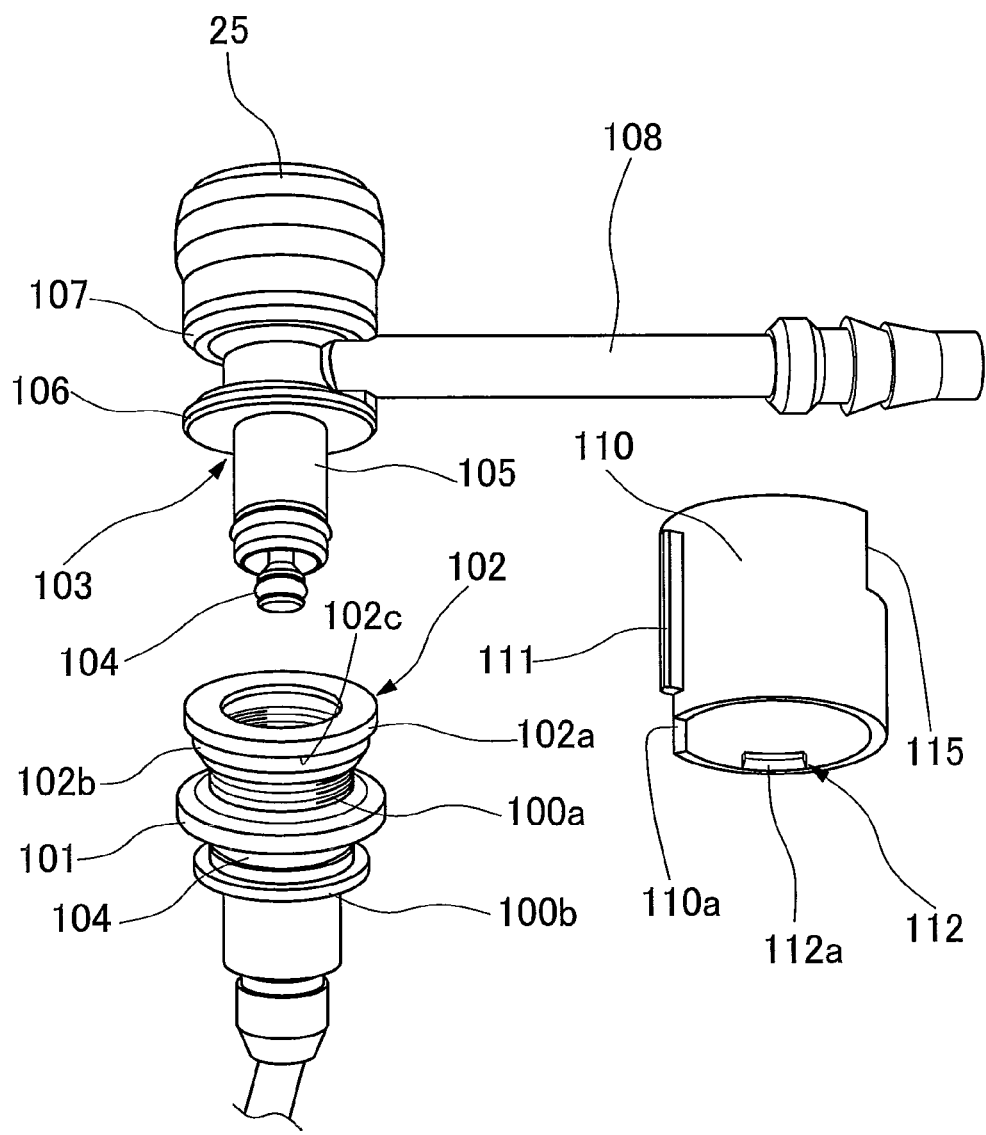
FIG. 11 is an exploded perspective view of the aspiration device in FIG. 10.

As shown in FIGS. 10 and 11, a valve casing 100 which is provided on a manipulating head 2 of an endoscope 1 is tapped with an external screw 100a on its outer peripheral surface, and an anchor nut 101 is threaded on the external screw 100a in such a way as to grip a housing 13 of the manipulating head 2 between the anchor nut 101 and a stopper flange 100b which is provided on the side of the valve casing 100. Threaded on the upper end of the valve casing 100 is a stationary flange member 102, which is formed with an upper large diameter portion 102a and a lower smaller diameter portion 102b on its outer peripheral side. The large and small diameter portions 102a and 102b are intervened by a transitory stepped wall surface 102c which is disposed perpendicularly to the center axis of the valve casing 100.

Substantially in the same way as in the foregoing first embodiment, a valve assembly unit 103 is composed of a valve guide member 104 and a valve member 105. The valve guide member 104 is formed with a detachable flange portion 206. At a predetermined distance from the detachable flange portion 106, a rim fitting portion 107 is provided on an upper portion of the valve guide member 104 to receive a rim portion at the lower end of a skirt portion of a dome-like aspiration trigger member 25. A connector pipe 108 is connected to a reduced diameter portion of the valve guide member 104 between the detachable flange portion 106 and the rim fitting portion 107.

The valve assembly unit 103 is coupled with the valve casing 100 by inserting a lower portion of the valve guide member 104 into the valve casing 100. A seal member 109 is interposed between the inserted lower portion of the valve guide member 104 and the valve casing 100. On insertion, the valve guide member 104 is pushed in until the detachable flange portion 106 comes into abutting engagement with the stationary flange member 102 on the side of the valve casing 100.

The valve assembly unit 103 is axially fixed to the valve casing 100, with the detachable flange portion 106 in abutting engagement with the stationary flange member 102. In this instance, a holder ring 110 is adopted for this purpose. The holder ring 110 is formed of a resilient material like metal or rubber, substantially in the shape of a round tube having a split portion 110a at one radial angular position to present a C-shape in cross section. In the proximity of the split portion 110a, the holder ring 110 is provided with expander tabs 111 which are prominently projected in a radially outward direction on the opposite sides of the split portion 110a. By spreading apart the expander tabs 111, the split portion 110a is widened through resilient deformation. Thus, the holder ring 110 returns to its original shape upon removing an external spreading force.

Figure 12:
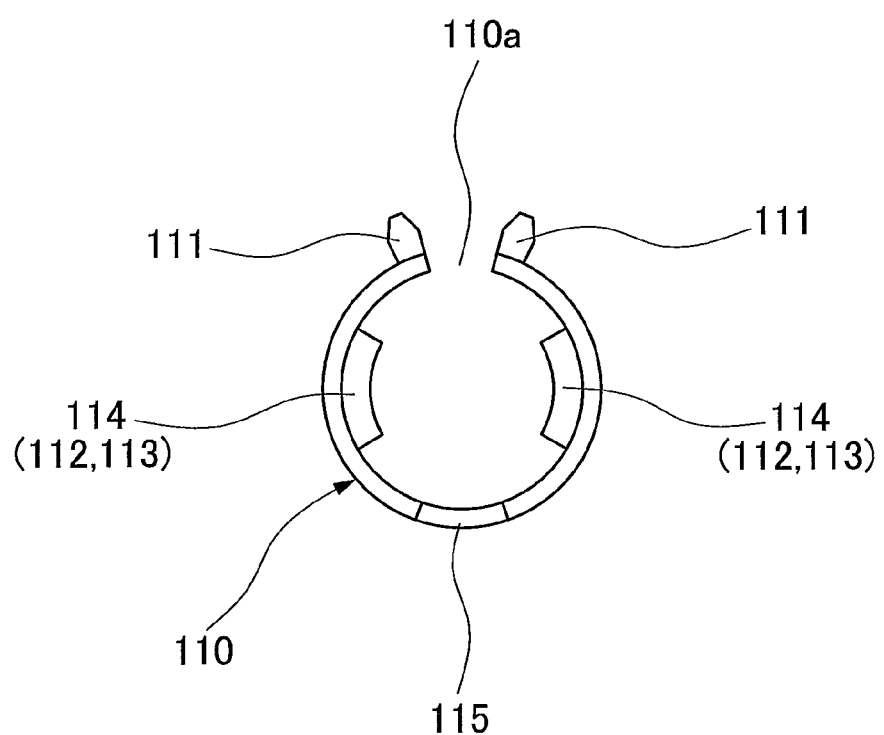
FIG. 12 is a schematic plan view of a holder ring.

As clear from FIG. 12, at diametrically opposite positions on the inner periphery of the holder ring 110, three sets of gripper ribs 112, 113 and 114 are projected in radially inward directions. Lowermost gripper ribs 112 are adapted to be brought into abutting engagement with the lower surface of the stationary flange member 102, while the intermediate gripper ribs 113 are adapted to be brought into abutting engagement with the top surface of the detachably flange portion 106 of the valve guide member 104. The uppermost gripper ribs 114 are adapted to be brought into abutting engagement with the valve manipulator mount portion 107 of the valve guide member 104. Thus, when the valve assembly unit 103 is assembled into the valve casing 100, the stationary flange member 102 and the detachable flange portion 106 are gripped fast to each other between the lower gripper ribs 112 and the intermediate gripper ribs 113.

Figure 13:
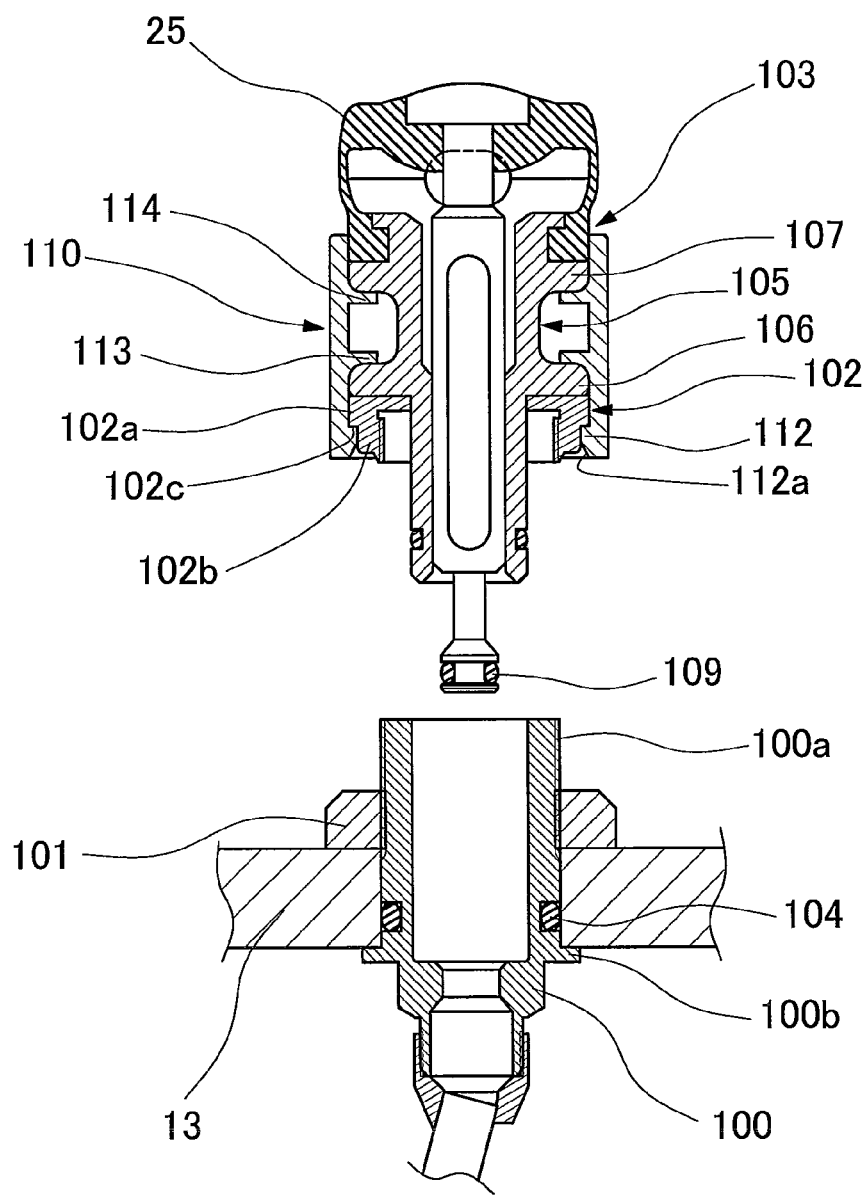
FIG. 13 is a schematic sectional view showing the holder ring which is fitted on a valve assembly unit in FIG. 10, which is disengaged and separated from a valve casing.

As mentioned above, the uppermost gripper ribs 114 are adapted to be brought into abutting engagement with the lower surface of the manipulator mount portion 107. As shown in FIG. 13, by the intermediate and uppermost gripper ribs 113 and 114, the holder ring 110 is fixedly retained on the valve assembly unit 103 even when the latter is separated from the valve casing 100. Therefore, the valve assembly unit 103, having the holder ring 110 fitted thereon beforehand, can be easily coupled with the valve casing 100 simply by pushing same into the valve casing 100 from above. In order to ensure smooth coupling of the valve assembly unit 103 with the valve casing 100, the lowermost gripper ribs 112 are each provided with a tapered surface 112a at a lower end, which is inclined radially outward in the downward direction. Thus, under the guidance of the inclined surfaces 112a, the lowermost gripper ribs 112 are urged to ride over the stationary flange member 102 and fit in position by a snap action.

Further, the holder ring 110 is provided with a notch 115 to a halfway point from its upper end to avoid interference with the connector pipe 109 which is extended radially outward from the valve guide member 104.

Figure 14:
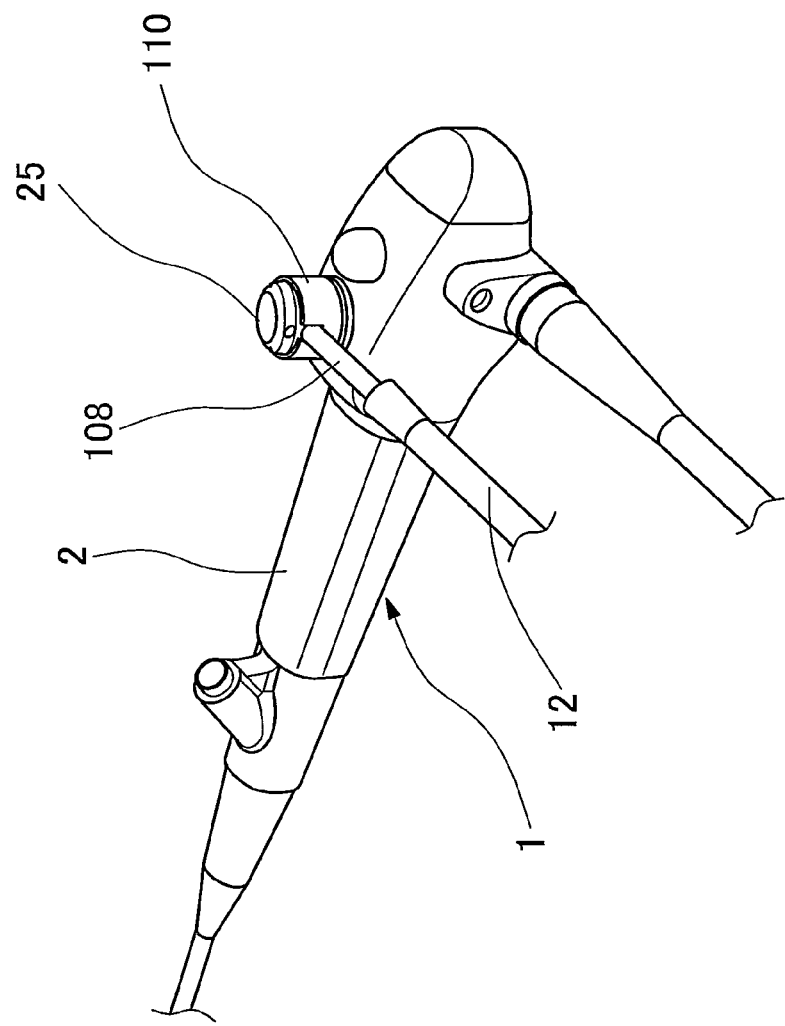
FIG. 14 is a schematic perspective view of an endoscope having the aspiration device fitted on its manipulating head.

By adoption of the construction as described above, the valve assembly unit 104 can be assembled with the valve casing 100 by means of the holder ring 110 as shown in FIG. 14. In this state, the stationary flange member 102 which is provided integrally on the side of the valve casing 100 is securely gripped between the lowermost and intermediate gripper ribs 112 and 113 of the holder ring 110 together with the detachable flange portion 106 on the side of the valve guide member 104 of the valve assembly unit 104. Thus, there is no possibility of the valve assembly unit 103 getting detached from the valve casing 100 during manipulation of the endoscope 1.

Further, at the time of disconnecting the valve assembly unit 104 including the proximal aspiration passage 12 from the valve casing 100 after use for washing purposes, for example, the holder ring 110 can be detached from the valve assembly unit 104 by pushing the expander tabs 111 away from each other to spread the split portion 110a wider. Thus, in this manner the valve assembly unit 104 is easily separable from the valve casing 100.

As described above, by spreading the split portion 110a in the holder ring 110, the valve assembly unit 104 can be separated from the valve casing 100. In this regard, the width of the split portion 110a must be smaller than 180 degrees, but it is possible to employ a relatively narrow split portion 110a form the standpoint of enhancing the stability in assembled state or to employ a relative relatively wide split portion 110a from the standpoint of facilitating its attachment and detachment.

The invention claimed is:

1. An endoscopic aspiration device for use on a manipulating head of an endoscope, to which a proximal end of an elongated insertion rod member is connected, said endoscopic aspiration device comprising a valve casing provided on said manipulating head in communication with an aspiration passage leading to a fore distal end of said insertion rod member, and a valve assembly unit composed of an assembly of a valve member and a valve guide member having a connector member extended out for connection to a proximal aspiration passage on the side of a suction source, said valve member being put in a sliding displacement along said valve guide member to bring said aspiration passage into and out of communication with said proximal aspiration passage, characterized in that said endoscopic aspiration device comprises:

a coupling mechanism provided between said valve casing and said valve guide member of said valve assembly unit and adapted to couple said valve guide member with said valve casing in such a way as to permit said valve assembly unit to make turns about a center axis of said valve casing on said manipulating head when said valve casing and said valve guide member are coupling; and said coupling mechanism including a coupling/uncoupling mechanism with a function of bringing said valve guide member of said valve assembly unit into and out of fitting engagement with said valve casing, and a lock-in mechanism with a function of retaining said valve guide member in a coupled state within the valve casing, preventing spontaneous dislodgement of said valve assembly unit from said valve casing, wherein said coupling/uncoupling mechanism includes an annular guide groove in one coupling portion on the side of said valve casing or on the side of said valve guide member, a locking projection provided on the other coupling portion on the side of said valve casing or on the side of said valve guide member, said locking projection being slidable in and along said guide groove, and an introductory groove provided in said one coupling portion in contiguously overlapped relation with an entrance to said guide groove, and said lock-in mechanism being arranged to limit angular range of sliding movement of said locking projection, prohibiting same from making a sliding displacement as far as an axially overlapping position relative to said introductory groove, and said guide groove and introductory groove are formed contiguously on an inner periphery of said valve casing while said locking projection is provided on an outer periphery of said valve guide member, and said connector member is in the form of a rigid pipe and projected radially outward from a lateral side of said valve assembly unit, said endoscopic aspiration device further comprising a manual push button switch provided on a casing of said manipulating head and projected to such a height as to interfere with said connector member when said valve guide member is turned in said valve casing in a direction toward said push button switch to perform the function of said lock-in mechanism, said push button switch being depressible to a reduced height, letting said connector member pass thereover and permitting said locking projection to slide as far as an axially overlapping position relative to said introductory groove to perform the function of said coupling/uncoupling mechanism.

2. An endoscopic aspiration device as set forth in claim 1, wherein said lock-in mechanism is adapted to limit a sliding movement of said locking projection toward an axially overlapping position relative to said introductory groove as long as said connector member is extended to the left of said manipulating head from said valve assembly unit, while said coupling/uncoupling mechanism is adapted to permit a sliding movement of said locking projection to an axially aligned overlapping position relative to said introductory groove when said connector member is turned to the right of said manipulating head.

3. An endoscopic aspiration device as set forth in claim 2, wherein said locking projection is brought to an axially aligned overlapping position relative to said introductory groove by a turning movement at least partly including a position where said connector member comes to overlapped relation with said push button switch.

4. An endoscopic aspiration device as set forth in claim 2, wherein said valve assembly unit is turnable in said valve casing along an arcuate guide groove between a first limit point where said connector member is abutted against said push button switch and a second limit point where said guide groove is blocked by a stopper wall, within an angular range defined by said first and second limit points on one side of said manipulating head, in opposingly confronting relation with said introductory groove located in another angular range defined by said first and second limit points on the opposite side of said manipulating head.

5. An endoscopic aspiration device for use on a manipulating head of an endoscope, to which a proximal end of an elongated insertion rod member is connected, said endoscopic aspiration device comprising a valve casing provided on said manipulating head in communication with an aspiration passage leading to a fore distal end of said insertion rod member, and a valve assembly unit composed of an assembly of a valve member and a valve guide member having a connector member extended out for connection to a proximal aspiration passage on the side of a suction source, said valve member being put in a sliding displacement along said valve guide member to bring said aspiration passage into and out of communication with said proximal aspiration passage, characterized in that said endoscopic aspiration device comprises:
  a coupling mechanism provided between said valve casing and said valve guide member of said valve assembly unit and adapted to couple said valve guide member with said valve casing in such a way as to permit said valve assembly unit to make turns about a center axis of said valve casing on said manipulating head when said valve casing and said valve guide member are coupling; and
  said coupling mechanism including a coupling/uncoupling mechanism with a function of bringing said valve guide member of said valve assembly unit into and out of fitting engagement with said valve casing, and a lock-in mechanism with a function of retaining said valve guide member in a coupled state within the valve casing, preventing spontaneous dislodgement of said valve assembly unit from said valve casing, wherein
  said coupling/uncoupling mechanism includes an annular guide groove in one coupling portion on the side of said valve casing or on the side of said valve guide member, a locking projection provided on the other coupling portion on the side of said valve casing or on the side of said valve guide member, said locking projection being slidable in and along said guide groove, and an introductory groove provided in said one coupling portion in contiguously overlapped relation with an entrance to said guide groove, and said lock-in mechanism being arranged to limit angular range of sliding movement of said locking projection, prohibiting same from making a sliding displacement as far as an axially overlapping position relative to said introductory groove, and said locking projection is provided virtually on an opposite side away from said connector member extended side, and said introductory groove is formed on said connector member extended side, wherein
  said guide groove and introductory groove are formed contiguously on an inner periphery of said valve casing while said locking projection is provided on an outer periphery of said valve guide member, and said connector member is in the form of a rigid pipe and projected radially outward from a lateral side of said valve assembly unit,
  said endoscopic aspiration device further comprising a manual push button switch provided on a casing of said manipulating head and projected to such a height as to interfere with said connector member when said valve guide member is turned in said valve casing in a direction toward said push button switch to perform the function of said lock-in mechanism, said push button switch being depressible to a reduced height, letting said connector member pass thereover and permitting said locking projection to slide as far as an axially overlapping position relative to said introductory groove to perform the function of said coupling/uncoupling mechanism.

6. An endoscopic aspiration device as set forth in claim 5, wherein said lock-in mechanism is adapted to limit a sliding movement of said locking projection toward an axially overlapping position relative to said introductory groove as long as said connector member is extended to the left of said manipulating head from said valve assembly unit, while said coupling/uncoupling mechanism is adapted to permit a sliding movement of said locking projection to an axially aligned overlapping position relative to said introductory groove when said connector member is turned to the right of said manipulating head.

7. An endoscopic aspiration device as set forth in claim 6, wherein said locking projection is brought to an axially aligned overlapping position relative to said introductory groove by a turning movement at least partly including a position where said connector member comes to overlapped relation with said push button switch.

8. An endoscopic aspiration device as set forth in claim 6, wherein said valve assembly unit is turnable in said valve casing along an arcuate guide groove between a first limit point where said connector member is abutted against said push button switch and a second limit point where said guide groove is blocked by a stopper wall, within an angular range defined by said first and second limit points on one side of said manipulating head, in opposingly confronting relation with said introductory groove located in another angular range defined by said first and second limit points on the opposite side of said manipulating head.

* * * * *